US009090906B2

(12) United States Patent
Soberon-Chavez et al.

(10) Patent No.: US 9,090,906 B2
(45) Date of Patent: Jul. 28, 2015

(54) **MUTANT *BACILLUS THURINGIENSIS* CRY GENES AND METHODS OF USE**

(75) Inventors: Mario Soberon-Chavez, Cuernavaca (MX); Alejandra Bravo-De La Parra, Cuernavaca (MX); Isabel Gomez-Gomez, Mexico City (MX)

(73) Assignee: UNIVERSIDAD NACIONAL AUTONOMA DE MEXICO (MX)

( * ) Notice: Subject to any disclaimer, the term of this patent is extended or adjusted under 35 U.S.C. 154(b) by 530 days.

(21) Appl. No.: 13/435,586

(22) Filed: Mar. 30, 2012

(65) Prior Publication Data

US 2012/0255071 A1    Oct. 4, 2012

Related U.S. Application Data

(60) Provisional application No. 61/469,380, filed on Mar. 30, 2011.

(51) Int. Cl.
*C12N 15/82* (2006.01)
*C07K 14/325* (2006.01)

(52) U.S. Cl.
CPC .......... *C12N 15/8286* (2013.01); *C07K 14/325* (2013.01)

(58) Field of Classification Search
None
See application file for complete search history.

(56) References Cited

U.S. PATENT DOCUMENTS

| 5,246,852 | A | * | 9/1993 | Payne et al. ............. 435/252.31 |
| 5,366,892 | A | | 11/1994 | Foncerrada et al. |
| 5,593,881 | A | | 1/1997 | Thompson et al. |
| 5,723,756 | A | | 3/1998 | Peferoen et al. |
| 5,747,450 | A | | 5/1998 | Ohba et al. |
| 5,840,868 | A | | 11/1998 | Warren et al. |
| 5,942,664 | A | | 8/1999 | Baum et al. |
| 2012/0210462 | A1 | | 8/2012 | Bermudez et al. |

FOREIGN PATENT DOCUMENTS

WO     WO 99/24581 A2    5/1999
WO     WO 2009/132850 A1    11/2009

OTHER PUBLICATIONS

Gomez et al 2006 The Journal of Biological Chemistry 281(45): 34032-34039.*
Atsumi et al 2005 Applied and Environmental Microbiology 71(7): 3966-3977.*
De Maagd et al 1999 Applied and Environmental Microbiology 65(10): 4369-4374.*
Herrero et al 2004 Biochemistry Journal 384: 507-513.*
Atsumi, S., et al., "Location of the *Bombyx mori* Aminopeptidase N Type 1 Binding Site on *Bacillus thuringiensis* Cry1AaToxin," *Applied and Environmental Microbiology*, 2005, vol. 71(7), pp. 3966-3977.
Avisar, D., et al., "The Role of *Bacillus thuringiensis* Cry1C and Cry1E Separate Structural Domains in the Interaction with *Spodoptera littoralis* Gut Epithelial Cells," *The Journal of Biological Chemistry*, 2004, vol. 279(16), pp. 15779-15786.
De Maagd, R., et al., "Domain III Substitution in *Bacillus thuringiensis* Delta-Endotoxin Cry1A(b) Results in Superior Toxicity for *Spodoptera exigua* and Altered Membrane Protein Recognition," *Applied and Environmental Microbiology*, 1996, vol. 62(5), pp. 1537-1543.
DeMaagd., R., et al., "How *Bacillus thuringiensis* has evolved specific toxins to colonize the insect world," *TRENDS in Genetics*, 2001,vol. 17(4), pp. 193-199.
Del Rincón-Castro, M., et al., "Antagonism between Cry1Ac1 and Cyt1A1 Toxins of *Bacillus thuringiensis*," *Applied and Environmental Microbiology*, 1999, vol. 65(5), pp. 2049-2053.
Environmental Protection Agency, "*Bacillus thuringiensis* Cry1Ab protein and the genetic material necessary for its production (pTDL004 or pTDL008) in Event T303-3 or T304-40 cotton plants (006525) Experimental Use Permit Fact Sheet," 2006, pp. 1-3, .epa.gov/oppbppd1/biopesticides/ingredients/factsheets/factsheet_006525.htm.
Environmental Protection Agency, "*Bacillus thuringiensis* delta endotoxins (Cry1Ac and Cry1C) encapsulated in killed *Pseudomonas fluorescens* (006457) Fact Sheet," 2010, pp. 1-2, .epa.gov/oppbppd1/biopesticides/ingredients/factsheets/factsheet_006457.
GenBank Accession No. M13898.1, "*B. thuringiensis* (berliner) crystalline entomocidal protoxin gene, complete cds," 1993, 2 pages.
GenBank Accession No. AAA22336.1, "delta-endotoxin, partial [*Bacillus thuringiensis*]," 1993, 1 page.
GenBank Accession No. AAA22541.1, "insecticidal crystal protein [*Bacillus thuringiensis*]," 1993, 1 page.
GenBank Accession No. AAA22542.1, "insect control protein [*Bacillus thuringiensis*]," 1993, 1 page.
GenBank Accession No. AAA22334.1, "cryIIIB2 [*Bacillus thuringiensis*]," 1993, 1 page.
GenBank Accession No. AAC43266.1, "CryIIIA [*Bacillus thuringiensis*]," 1994, 2.
GenBank Accession No. AAA74198.1, "Cry3Bb2 [*Bacillus thuringiensis*]," 1995, 1 page.
GenBank Accession No. I15475.1, "Sequence 2 from patent US 5466597," 1996, 1 page.
GenBank Accession No. AAA50255.1, "crystal protein [*Bacillus thuringiensis* serovar morrisoni]," 2002, 1 page.
GenBank Accession No. AAS79487.1, "insecticidal crystal protein [*Bacillus thuringiensis*]," 2004, 1 page.
GenBank Accession No. AAW05659.1, "Sequence 2 from patent US 6797490," 2004, 1 page.
GenBank Accession No. AY955268.1, "*Bacillus thuringiensis* insecticidal crystal protein Cry1C (cry1Ca) gene, complete cds," 2005, 3 pages.
GenBank Accession No. CAA68482.1, "unnamed protein product [*Bacillus thuringiensis*]," 2005, 1 page.

(Continued)

*Primary Examiner* — David H Kruse
(74) *Attorney, Agent, or Firm* — Ballard Spahr LLP

(57) ABSTRACT

The invention provides nucleic acids obtained from strains of *Bacillus thuringiensis* encoding δ-endotoxins having pesticidal activity against insect pests including Lepidoptera. Particular embodiments of the invention provide isolated nucleic acid molecules encoding mutant pesticidal polypeptides, pesticidal compositions, expression cassettes, and transformed microorganisms and plants comprising a nucleic acid molecule of the invention. Such compositions find use in methods for controlling plant pests.

37 Claims, No Drawings

(56) References Cited

OTHER PUBLICATIONS

GenBank Accession No. CAB41411.1, "Cry3Aa protein [*Bacillus thuringiensis*]," 2005, 2 pages.

GenBank Accession No. AAU29411.1, "Cry3Aa protein [*Bacillus thuringiensis*]," 2005, 1 page.

GenBank Accession No. AAW82872.1, "Cry3 delta endotoxin [*Bacillus thuringiensis* serovar tenebrionis]," 2005, 1 page.

GenBank Accession No. CAA34983.1, "unnamed protein product, partial [*Bacillus thuringiensis*]," 2005, 2 pages.

GenBank Accession No. CAA00645.1, "toxin [*Bacillus thuringiensis*]," 2005, 1 page.

GenBank Accession No. CAA42469.1, "CryIIID [*Bacillus thuringiensis* serovar kurstaki]," 2005, 2 pages.

GenBank Accession No. ABY49136.1, "Cry3A [*Bacillus thuringiensis* serovar tenebrionis]," 2008, 2 pages.

Gómez, I., et al., "Specific Epitopes of Domains II and III of *Bacillus thuringiensis* Cry1Ab Toxin Involved in the Sequential Interaction with Cadherin and Aminopeptidase-N Receptors in *Manduca sexta*," *The Journal of Biological Chemistry*, 2006, vol. 281(45).

Gómez, I., et al., "New Insights into the Mode of Action of Cry1Ab Toxin used in Transgenic Insect-Resistant Crops," *Southwestern Entomologist*, 2010, vol. 35(3), pp. 387-390.

Karim, S., et al., "Pesticidal and Receptor Binding Properties of *Bacillus thuringiensis* Cry1Ab and Cry1Ac δ-Endotoxin Mutants to *Pectinophora gossypiella* and *Helicoverpa zea*," *Current Microbiology*, 2000, vol. 41, pp. 430-440.

Lee, M., et al., "Identification of Residues in Domain III of *Bacillus thuringiensis* Cry1Ac Toxin That Affect Binding and Toxicity," *Applied and Environmental Microbiology*, 1999, vol. 65(10), pp. 4513-4520.

Nakanishi, K., et al., "Aminopeptidase N isoforms from the midgut of *Bombyx mori* and *Plutella xylostella*—their classification and the factors that determine their binding specificity to *Bacillus thuringiensis* Cry1A toxin," *FEBS Letters*, 2002, vol. 519, pp. 215-220.

Pardo-López, L., et al., "Strategies to improve the insecticidal activity of Cry toxins from *Bacillus thuringiensis*," *Peptides*, 2009, vol. 30, pp. 589-595.

Saraswathy, N., et al., "Protein engineering of δ-endotoxins of *Bacillus thuringiensis*," *Electronic Journal of Biotechnology*, 2004, vol. 7(2), pp. 180-190.

Van Rie, J., et al., "Receptors on the Brush Border Membrane of the Insect Midgut as Determinants of the Specificity of *Bacillus thuringiensis* Delta-Endotoxins," *Applied and Environmental Microbiology*, 1990, vol. 56(5), pp. 1378-1385.

Yaoi, K., et al., "*Bacillus thuringiensis* Cry1Aa toxin-binding region of *Bombyx mori* aminopeptidase N," *FEBS Letters*, 1999, vol. 463, pp. 221-224.

\* cited by examiner

SEQUENCE LISTING

<160> NUMBER OF SEQ ID NOS: 12

<210> SEQ ID NO 1
<211> LENGTH: 3778
<212> TYPE: DNA
<213> ORGANISM: Bacillus thuringiensis

<400> SEQUENCE: 1

```
tcaaaaattg atatttagta aaattagttg cactttgtgc atttttttcat aagatgagtc      60
atatgtttta aattgtagta atgaaaaaca gtattatatc ataatgaatt ggtatcttaa     120
taaaagagat ggaggtaact tatggataac aatccgaaca tcaatgaatg cattccttat     180
aattgtttaa gtaaccctga agtagaagta ttaggtggag aaagaataga aactggttac     240
accccaatcg atatttcctt gtcgctaacg caatttcttt tgagtgaatt tgttcccggt     300
gctggatttg tgttaggact agttgatata atatggggaa tttttggtcc ctctcaatgg     360
gacgcatttc ttgtacaaat tgaacagtta attaaccaaa gaatagaaga attcgctagg     420
aaccaagcca tttctagatt agaaggacta agcaatcttt atcaaattta cgcagaatct     480
tttagagagt gggaagcaga tcctactaat ccagcattaa gagaagagat gcgtattcaa     540
ttcaatgaca tgaacagtgc ccttacaacc gctattcctc tttttgcagt tcaaaattat     600
caagttcctc ttttatcagt atatgttcaa gctgcaaatt tacatttatc agttttgaga     660
gatgtttcag tgtttggaca aaggtgggga tttgatgccg cgactatcaa tagtcgttat     720
aatgatttaa ctaggcttat tggcaactat acagatcatg ctgtacgctg gtacaatacg     780
ggattagagc gtgtatgggg accggattct agagattgga taagatataa tcaatttaga     840
agagaattaa cactaactgt attagatatc gtttctctat ttccgaacta tgatagtaga     900
acgtatccaa ttcgaacagt ttcccaatta acaagagaaa tttatacaaa cccagtatta     960
gaaaattttg atggtagttt tcgaggctcg gctcagggca tagaaggaag tattaggagt    1020
ccacatttga tggatatact taacagtata accatctata cggatgctca tagaggagaa    1080
tattattggt cagggcatca aataatggct tctcctgtag ggttttcggg gccagaattc    1140
acttttccgc tatatggaac tatgggaaat gcagctccac aacaacgtat tgttgctcaa    1200
ctaggtcagg gcgtgtatag aacattatcg tccactttat atagaagacc ttttaatata    1260
gggataaata atcaacaact atctgttctt gacgggacag aatttgctta tggaacctcc    1320
tcaaatttgc catccgctgt atacagaaaa agcggaacgg tagattcgct ggatgaaata    1380
ccgccacaga ataacaacgt gccacctagg caaggattta gtcatcgatt aagccatgtt    1440
tcaatgtttc gttcaggctt tagtaatagt agtgtaagta taataagagc tcctatgttc    1500
tcttggatac atcgtagtgc tgaatttaat aatataattc cttcatcaca aattacacaa    1560
atacctttaa caaaatctac taatcttggc tctggaactt ctgtcgttaa aggaccagga    1620
tttacaggag gagatattct tcgaagaact tcacctggcc agatttcaac cttaagagta    1680
aatattactg caccattatc acaaagatat cgggtaagaa ttcgctacgc ttctaccaca    1740
aatttacaat tccatacatc aattgacgga agacctatta atcaggggaa tttttcagca    1800
actatgagta gtgggagtaa tttacagtcc ggaagcttta ggactgtagg ttttactact    1860
ccgtttaact tttcaaatgg atcaagtgta tttacgttaa gtgctcatgt cttcaattca    1920
ggcaatgaag tttatataga tcgaattgaa tttgttccgg cagaagtaac ctttgaggca    1980
gaatatgatt tagaaagagc acaaaaggcg gtgaatgagc tgtttacttc ttccaatcaa    2040
atcgggttaa aaacagatgt gacggattat catattgatc aagtatccaa tttagttgag    2100
```

```
tgtttatctg atgaattttg tctggatgaa aaaaaagaat tgtccgagaa agtcaaacat    2160
gcgaagcgac ttagtgatga gcggaattta cttcaagatc caaactttag agggatcaat    2220
agacaactag accgtggctg gagaggaagt acggatatta ccatccaagg aggcgatgac    2280
gtattcaaag agaattacgt tacgctattg ggtaccttg atgagtgcta tccaacgtat    2340
ttatatcaaa aaatagatga gtcgaaatta aaagcctata cccgttacca attaagaggg    2400
tatatcgaag atagtcaaga cttagaaatc tatttaattc gctacaatgc caaacacgaa    2460
acagtaaatg tgccaggtac gggttcctta tggccgcttt cagccccaag tccaatcgga    2520
aaatgtgccc atcattccca tcatttctcc ttggacattg atgttggatg tacagactta    2580
aatgaggact taggtgtatg ggtgatattc aagattaaga cgcaagatgg ccatgcaaga    2640
ctaggaaatc tagaatttct cgaagagaaa ccattagtag gagaagcact agctcgtgtg    2700
aaaagagcgg agaaaaaatg gagagacaaa cgtgaaaaat tggaatggga aacaaatatt    2760
gtttataaag aggcaaaaga atctgtagat gctttatttg taaactctca atatgataga    2820
ttacaagcgg ataccaacat cgcgatgatt catgcggcag ataaacgcgt tcatagcatt    2880
cgagaagctt atctgcctga gctgtctgtg attccgggtg tcaatgcggc tattttttgaa    2940
gaattagaag ggcgtatttt cactgcattc tccctatatg atgcgagaaa tgtcattaaa    3000
aatggtgatt ttaataatgg cttatcctgc tggaacgtga agggcatgt agatgtagaa    3060
gaacaaaaca accaccgttc ggtccttgtt gttccggaat gggaagcaga agtgtcacaa    3120
gaagttcgtg tctgtccggg tcgtggctat atccttcgtg tcacagcgta caaggaggga    3180
tatggagaag gttgcgtaac cattcatgag atcgagaaca atacagacga actgaagttt    3240
agcaactgtg tagaagagga agtatatcca aacaacacgg taacgtgtaa tgattatact    3300
gcgactcaag aagaatatga gggtacgtac acttctcgta atcgaggata tgacggagcc    3360
tatgaaagca attcttctgt accagctgat tatgcatcag cctatgaaga aaaagcatat    3420
acagatggac gaagagacaa tccttgtgaa tctaacagag gatatgggga ttacacacca    3480
ctaccagctg gctatgtgac aaaagaatta gagtacttcc cagaaaccga taaggtatgg    3540
attgagatcg gagaaacgga aggaacattc atcgtggaca gcgtggaatt acttcttatg    3600
gaggaataat atatgcttta aaatgtaagg tgtgcaaata aagaatgatt actgacttgt    3660
attgacagat aaaataagga atttttatat gaataaaaaa cgggcatcac tcttaaaaga    3720
atgatgtccg tttttgtat gatttaacga gtgatattta aatgtttttt tgcgaagg      3778
```

<210> SEQ ID NO 2
<211> LENGTH: 1155
<212> TYPE: PRT
<213> ORGANISM: Bacillus thuringiensis

<400> SEQUENCE: 2

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

-continued

Glu Gln Leu Ile Asn Gln Arg Ile Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
    435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
            565                 570                 575

Phe Ser Asn Gly Ser Ser Val Phe Thr Leu Ser Ala His Val Phe Asn
        580                 585                 590

Ser Gly Asn Glu Val Tyr Ile Asp Arg Ile Glu Phe Val Pro Ala Glu
    595                 600                 605

Val Thr Phe Glu Ala Glu Tyr Asp Leu Glu Arg Ala Gln Lys Ala Val
610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
            645                 650                 655

Asp Glu Phe Cys Leu Asp Glu Lys Lys Glu Leu Ser Glu Lys Val Lys
        660                 665                 670

His Ala Lys Arg Leu Ser Asp Glu Arg Asn Leu Leu Gln Asp Pro Asn
    675                 680                 685

Phe Arg Gly Ile Asn Arg Gln Leu Asp Arg Gly Trp Arg Gly Ser Thr
690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
            725                 730                 735

Lys Ile Asp Glu Ser Lys Leu Lys Ala Tyr Thr Arg Tyr Gln Leu Arg
        740                 745                 750

Gly Tyr Ile Glu Asp Ser Gln Asp Leu Glu Ile Tyr Leu Ile Arg Tyr
    755                 760                 765

Asn Ala Lys His Glu Thr Val Asn Val Pro Gly Thr Gly Ser Leu Trp
770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
            805                 810                 815

Leu Gly Val Trp Val Ile Phe Lys Ile Lys Thr Gln Asp Gly His Ala
        820                 825                 830

Arg Leu Gly Asn Leu Glu Phe Leu Glu Glu Lys Pro Leu Val Gly Glu
    835                 840                 845

Ala Leu Ala Arg Val Lys Arg Ala Glu Lys Lys Trp Arg Asp Lys Arg
850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
            885                 890                 895

Asp Thr Asn Ile Ala Met Ile His Ala Ala Asp Lys Arg Val His Ser
        900                 905                 910

Ile Arg Glu Ala Tyr Leu Pro Glu Leu Ser Val Ile Pro Gly Val Asn

-continued

```
        915                 920                 925

Ala Ala Ile Phe Glu Glu Leu Glu Gly Arg Ile Phe Thr Ala Phe Ser
    930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
            980                 985                 990

Gln Glu Val Arg Val Cys Pro Gly  Arg Gly Tyr Ile Leu  Arg Val Thr
        995                 1000                1005

Ala Tyr  Lys Glu Gly Tyr Gly  Glu Gly Cys Val Thr  Ile His Glu
    1010                1015                1020

Ile Glu  Asn Asn Thr Asp Glu  Leu Lys Phe Ser Asn  Cys Val Glu
    1025                1030                1035

Glu Glu  Val Tyr Pro Asn Asn  Thr Val Thr Cys Asn  Asp Tyr Thr
    1040                1045                1050

Ala Thr  Gln Glu Glu Tyr Glu  Gly Thr Tyr Thr Ser  Arg Asn Arg
    1055                1060                1065

Gly Tyr  Asp Gly Ala Tyr Glu  Ser Asn Ser Ser Val  Pro Ala Asp
    1070                1075                1080

Tyr Ala  Ser Ala Tyr Glu Glu  Lys Ala Tyr Thr Asp  Gly Arg Arg
    1085                1090                1095

Asp Asn  Pro Cys Glu Ser Asn  Arg Gly Tyr Gly Asp  Tyr Thr Pro
    1100                1105                1110

Leu Pro  Ala Gly Tyr Val Thr  Lys Glu Leu Glu Tyr  Phe Pro Glu
    1115                1120                1125

Thr Asp  Lys Val Trp Ile Glu  Ile Gly Glu Thr Glu  Gly Thr Phe
    1130                1135                1140

Ile Val  Asp Ser Val Glu Leu  Leu Leu Met Glu Glu
    1145                1150                1155
```

<210> SEQ ID NO 3
<211> LENGTH: 3135
<212> TYPE: DNA
<213> ORGANISM: Bacillus thuringiensis

<400> SEQUENCE: 3

```
atggaggaaa ataatcaaaa tcaatgcata ccttacaatt gtttaagtaa tcctgaagaa     60
gtacttttgg atggagaacg gatatcaact ggtaattcat caattgatat ttctctgtca    120
cttgttcagt ttctggtatc taactttgta ccagggggag gatttttagt tggattaata    180
gattttgtat ggggaatagt tggcccttct caatgggatg catttctagt acaaattgaa    240
caattaatta atgaaagaat agctgaattt gctaggaatg ctgctattgc taatttagaa    300
ggattaggaa acaatttcaa tatatatgtg gaagcattta aagaatggga agaagatcct    360
aataatccag caaccaggac cagagtaatt gatcgctttc gtatacttga tgggctactt    420
gaaagggaca ttccttcgtt tcgaatttct ggatttgaag taccccttt atccgtttat     480 gctcaagcgg ccaatctgca tctagctata ttaagagatt ctgtaatttt tggagaaaga    540
tggggattga caacgataaa tgtcaatgaa aactataata gactaattag gcatattgat    600
gaatatgctg atcactgtgc aaatacgtat aatcggggat taaataattt accgaaatct    660
acgtatcaag attggataac atataatcga ttacggagag acttaacatt gactgtatta    720
```

```
gatatcgccg ctttctttcc aaactatgac aataggagat atccaattca gccagttggt    780
caactaacaa gggaagttta tacggaccca ttaattaatt ttaatccaca gttacagtct    840
gtagctcaat tacctacttt taacgttatg gagagcagcg caattagaaa tcctcattta    900
tttgatatat tgaataatct tacaatcttt acggattggt ttagtgttgg acgcaatttt    960
tattggggag gacatcgagt aatatctagc cttataggag gtggtaacat aacatctcct   1020
atatatggaa gagaggcgaa ccaggagcct ccaagatcct ttactttaa tggaccggta    1080 tttaggactt tatcaaatcc tactttacga ttattacagc aaccttggcc agcgccacca   1140
tttaatttac gtggtgttga aggagtagaa ttttctacac ctacaaatag ctttacgtat   1200
cgaggaagag gtacggttga ttcttaact gaattaccgc ctgaggataa tagtgtgcca    1260
cctcgcgaag gatatagtca tcgtttatgt catgcaactt ttgttcaaag atctggaaca   1320
ccttttttaa caactggtgt agtattttct tggacgcatc gtagtgcaac tcttacaaat   1380
acaattgatc cagagagaat taatcaaata cctttagtga aaggatttag agtttggggg   1440
ggcacctctg tcattacagg accaggattt acaggagggg atatccttcg aagaaatacc   1500
tttggtgatt ttgtatctct acaagtcaat attaattcac caattaccca agataccgt    1560 ttaagatttc gttacgcttc cagtagggat gcacgagtta tagtattaac aggagcggca   1620
tccacaggag tgggaggcca agttagtgta aatatgcctc ttcagaaaac tatggaaata   1680
ggggagaact taacatctag aacatttaga tataccgatt ttagtaatcc ttttcattt    1740 agagctaatc cagatataat tgggataagt gaacaacctc tatttggtgc aggttctatt   1800
agtagcggtg aactttatat agataaaatt gaaattattc tagcagatgc aacatttgaa   1860
gcagaatctg atttagaaag agcacaaaag gcggtgaatg ccctgtttac ttcttccaat   1920
caaatcgggt taaaaaccga tgtgacggat tatcatattg atcaagtatc caatttagtg   1980
gattgtttat cagatgaatt ttgtctggat gaaaagcgag aattgtccga gaaagtcaaa   2040
catgcgcagc gactcagtga tgagcggaat ttacttcaag atccaaactt cagagggatc   2100
aatagacaac cagaccgtgg ctggagagga agtacagata ttaccatcca aggaggagat   2160
gacgtattca agagaattaa cgtcacacta ccgggtaccg ttgatgagtg ctatccaacg   2220
tatttatatc agaaaataga tgagtcgaaa ttaaaagctt atacccgtta tgaattaaga   2280
gggtatatcg aagatagtca agacttagaa atctatttga tccgttacaa tgcaaaacac   2340
gaaatagtaa atgtgccagg cacgggttcc ttatggccgc tttcagccca agtccaatc    2400 ggaaagtgtg gagaaccgaa tcgatgcgcg ccacaccttg aatggaatcc tgatctagat   2460
tgttcctgca gagacgggga aaaatgtgca catcattccc atcatttcac cttggatatt   2520
gatgttggat gtacagactt aaatgaggac ttaggtgtat gggtgatatt caagattaag   2580
acgcaagatg gccatgcaag actagggaat ctagagtttc tcgaagagaa accattatta   2640
ggggaagcac tagctcgtgt gaaaagagcg gagaagaagt ggagagacaa acgagagaaa   2700
ctgcagttgg aaacaaatat tgtttataaa gaggcaaaag aatctgtaga tgctttattt   2760
gtaaactctc aatatgatag attacaagtg gatacgaaca tcgcaatgat tcatgcggca   2820
gataaacgcg ttcatagaat ccgggaagcg tatctgccag agttgtctgt gattccaggt   2880
gtcaatgcgg ccattttcga agaattagag ggacgtattt ttacagcgta ttccttatat   2940
gatgcgagaa atgtcattaa aaatggcgat ttcaataatg gcttattatg ctggaacgtg   3000
aaaggtcatg tagatgtaga gagcaaaac aaccaccgtt cggtccttgt tatcccagaa    3060
tgggaggcag aagtgtcaca agaggttcgt gtctgtccag gtcgtggcta tatccttcgt   3120
```
gtcacagcat attaa                                                        3135

<210> SEQ ID NO 4
<211> LENGTH: 1044
<212> TYPE: PRT
<213> ORGANISM: Bacillus thuringiensis

<400> SEQUENCE: 4

```
Met Glu Glu Asn Asn Gln Asn Gln Cys Ile Pro Tyr Asn Cys Leu Ser
 1               5                  10                  15

Asn Pro Glu Glu Val Leu Leu Asp Gly Glu Arg Ile Ser Thr Gly Asn
             20                  25                  30

Ser Ser Ile Asp Ile Ser Leu Ser Leu Val Gln Phe Leu Val Ser Asn
         35                  40                  45

Phe Val Pro Gly Gly Gly Phe Leu Val Gly Leu Ile Asp Phe Val Trp
     50                  55                  60

Gly Ile Val Gly Pro Ser Gln Trp Asp Ala Phe Leu Val Gln Ile Glu
 65                  70                  75                  80

Gln Leu Ile Asn Glu Arg Ile Ala Glu Phe Ala Arg Asn Ala Ala Ile
                 85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365
```

```
Leu Arg Leu Leu Gln Gln Pro Trp Pro Ala Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
                405                 410                 415

Asn Ser Val Pro Pro Arg Glu Gly Tyr Ser His Arg Leu Cys His Ala
                420                 425                 430

Thr Phe Val Gln Arg Ser Gly Thr Pro Phe Leu Thr Thr Gly Val Val
        435                 440                 445

Phe Ser Trp Thr His Arg Ser Ala Thr Leu Thr Asn Thr Ile Asp Pro
    450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
                500                 505                 510

Ser Pro Ile Thr Gln Arg Tyr Arg Leu Arg Phe Arg Tyr Ala Ser Ser
        515                 520                 525

Arg Asp Ala Arg Val Ile Val Leu Thr Gly Ala Ala Ser Thr Gly Val
530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
                580                 585                 590

Pro Leu Phe Gly Ala Gly Ser Ile Ser Ser Gly Glu Leu Tyr Ile Asp
        595                 600                 605

Lys Ile Glu Ile Ile Leu Ala Asp Ala Thr Phe Glu Ala Glu Ser Asp
    610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
                660                 665                 670

Arg Glu Leu Ser Glu Lys Val Lys His Ala Gln Arg Leu Ser Asp Glu
                675                 680                 685

Arg Asn Leu Leu Gln Asp Pro Asn Phe Arg Gly Ile Asn Arg Gln Pro
    690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
        740                 745                 750

Ala Tyr Thr Arg Tyr Glu Leu Arg Gly Tyr Ile Glu Asp Ser Gln Asp
        755                 760                 765

Leu Glu Ile Tyr Leu Ile Arg Tyr Asn Ala Lys His Glu Ile Val Asn
    770                 775                 780
```

-continued

```
Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
            805                 810                 815

Pro Asp Leu Asp Cys Ser Cys Arg Asp Gly Glu Lys Cys Ala His His
        820                 825                 830

Ser His His Phe Thr Leu Asp Ile Asp Val Gly Cys Thr Asp Leu Asn
    835                 840                 845

Glu Asp Leu Gly Val Trp Val Ile Phe Lys Ile Lys Thr Gln Asp Gly
850                 855                 860

His Ala Arg Leu Gly Asn Leu Glu Phe Leu Glu Lys Pro Leu Leu
865                 870                 875                 880

Gly Glu Ala Leu Ala Arg Val Lys Arg Ala Glu Lys Lys Trp Arg Asp
            885                 890                 895

Lys Arg Glu Lys Leu Gln Leu Glu Thr Asn Ile Val Tyr Lys Glu Ala
        900                 905                 910

Lys Glu Ser Val Asp Ala Leu Phe Val Asn Ser Gln Tyr Asp Arg Leu
    915                 920                 925

Gln Val Asp Thr Asn Ile Ala Met Ile His Ala Asp Lys Arg Val
930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
            965                 970                 975

Tyr Ser Leu Tyr Asp Ala Arg Asn Val Ile Lys Asn Gly Asp Phe Asn
        980                 985                 990

Asn Gly Leu Leu Cys Trp Asn Val Lys Gly His Val Asp Val Glu Glu
    995                 1000                1005

Gln Asn Asn His Arg Ser Val Leu Val Ile Pro Glu Trp Glu Ala
1010            1015                1020

Glu Val Ser Gln Glu Val Arg Val Cys Pro Gly Arg Gly Tyr Ile
1025            1030                1035

Leu Arg Val Thr Ala Tyr
    1040

<210> SEQ ID NO 5
<211> LENGTH: 4
<212> TYPE: PRT
<213> ORGANISM: Artificial Sequence
<220> FEATURE:
<223> OTHER INFORMATION: ER retention polypeptide

<400> SEQUENCE: 5

Lys Asp Glu Leu
1

<210> SEQ ID NO 6
<211> LENGTH: 6
<212> TYPE: PRT
<213> ORGANISM: Artificial Sequence
<220> FEATURE:
<223> OTHER INFORMATION: ER retention polypeptide

<400> SEQUENCE: 6

Ser Glu Lys Asp Glu Leu
1               5

<210> SEQ ID NO 7
```

```
<211> LENGTH: 4
<212> TYPE: PRT
<213> ORGANISM: Artificial Sequence
<220> FEATURE:
<223> OTHER INFORMATION: ER retention polypeptide

<400> SEQUENCE: 7

His Asp Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: ER retention polypeptide

<400> SEQUENCE: 8

His Asp Glu Phe
1

<210> SEQ ID NO 9
<211> LENGTH: 6
<212> TYPE: PRT
<213> ORGANISM: Bacillus thuringiensis

<400> SEQUENCE: 9

Ser Thr Leu Arg Val Asn
1               5

<210> SEQ ID NO 10
<211> LENGTH: 8
<212> TYPE: PRT
<213> ORGANISM: Bacillus thuringiensis

<400> SEQUENCE: 10

Val Phe Thr Leu Ser Ala His Val
1               5

<210> SEQ ID NO 11
<211> LENGTH: 12
<212> TYPE: PRT
<213> ORGANISM: Bacillus thuringiensis

<400> SEQUENCE: 11

Gly Gln Ile Ser Thr Leu Arg Val Asn Ile Thr Ala
1               5                   10

<210> SEQ ID NO 12
<211> LENGTH: 10
<212> TYPE: PRT
<213> ORGANISM: Bacillus thuringiensis

<400> SEQUENCE: 12

Val Phe Thr Leu Ser Ala His Val Phe Asn
1               5                   10
```

MUTANT *BACILLUS THURINGIENSIS* CRY GENES AND METHODS OF USE

CROSS-REFERENCE TO RELATED APPLICATIONS

This application claims the benefit of U.S. Provisional Application No. 61/469,380, filed Mar. 30, 2011, which is hereby incorporated herein in its entirety by reference.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 416876SEQLIST.txt, a creation date of Mar. 28, 2012 and a size of 29 kilobytes. The sequence listing filed via EFS-Web is part of the specification and is incorporated herein by reference as if set forth in its entirety.

FIELD OF THE INVENTION

The present invention relates to the fields of plant molecular biology and plant pest control. More particularly, the present invention relates to *Bacillus thuringiensis* Cry genes that encode δ-endotoxins characterized by pesticidal activity against insect pests. Compositions and methods of the invention utilize disclosed nucleic acids, and their encoded mutant pesticidal polypeptides, to control pests.

BACKGROUND OF THE INVENTION

Insect pests are a major factor in the loss of the world's agricultural crops. For example, fall armyworm or tobacco hornworm feeding damage can be economically devastating to agricultural producers. Insect pest-related crop loss from corn rootworm alone has reached one billion dollars a year in damage and control expenses.

Traditionally, the primary methods for impacting insect pest populations, such as corn rootworm populations, are crop rotation and the application of broad-spectrum synthetic chemical pesticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative. Generally speaking, the use of biopesticides presents a lower risk of pollution and environmental hazards, and provides greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* and *Bacillus papilliae* are among the most successful biocontrol agents discovered to date. Insect pathogenicity has been attributed to strains of: *B. larvae*, *B. lentimorbus*, *B. papilliae*, *B. sphaericus*, *B. thuringiensis* (Harwook, ed. (1989) *Bacillus* (Plenum Press), p. 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868). Microbial pesticides, particularly those obtained from *Bacillus* strains, have played an important role in agriculture as alternatives to chemical pest control. Pesticidal proteins isolated from strains of *Bacillus thuringiensis*, known as δ-endotoxins or Cry toxins, are initially produced in an inactive protoxin form. These protoxins are proteolytically converted into an active toxin through the action of proteases in the insect gut. See, Rukmini et al. (2000) *Biochimie* 82:109-116; Oppert (1999) *Arch. Insect Biochem. Phys.* 42:1-12; and Carroll et al. (1997) *J. Invertebrate Pathology* 70:41-49. Proteolytic activation of the toxin can include the removal of the N- and C-terminal peptides from the protein, as well as internal cleavage of the protein. Once activated, the Cry toxin binds with high affinity to receptors on epithelial cells in the insect gut, thereby creating leakage channels in the cell membrane, lysis of the insect gut, and subsequent insect death through starvation and septicemia. See, e.g., Li et al. (1991) *Nature* 353:815-821.

Recently, agricultural scientists have developed crop plants with enhanced insect resistance by genetically engineering crop plants with pesticidal genes to produce pesticidal proteins from *Bacillus*. For example, corn and cotton plants genetically engineered to produce Cry toxins (see, e.g., Aronson (2002) *Cell Mol. Life. Sci.* 59(3):417-425; Schnepf et al. (1998) *Microbiol. Mol. Biol. Rev.* 62(3):775-806) are now widely used in American agriculture and have provided the farmer with an environmentally friendly alternative to traditional insect-control methods. In addition, potatoes genetically engineered to contain pesticidal Cry toxins have been developed. While they have been proven to be very successful commercially, these genetically-engineered, insect-resistant crop plants provide resistance to only a narrow range of the economically important insect pests.

Accordingly, there remains a need for new Bt toxins with a broader range of insecticidal activity against insect pests, e.g., toxins which are active against a greater variety of insects from the order Lepidoptera. In addition, there remains a need for biopesticides having activity against a variety of insect pests and for biopesticides which have improved insecticidal activity.

SUMMARY OF THE INVENTION

Compositions and methods are provided for protecting a plant from a plant pest, particularly an insect pest. More particularly, this document provides compositions and methods for use in agriculture for controlling agriculturally significant pests of many crop plants such as, for example, the fall armyworm, e.g., *Spodoptera frugiperda*. The compositions comprise altered Cry nucleotide sequences and the polypeptides encoded by such sequences. The polypeptides are mutagenized or altered in domain III, the binding domain. The compositions include nucleic acid molecules encoding novel mutant members of the Cry family of δ-endotoxins that have pesticidal activity against insect pests. As examples, Cry1Ab and Cry1C altered polypeptides having particular amino acid substitutions in domain III are provided. The altered polypeptides display toxin activity against additional pests and increased insecticidal activity. For Cry1Ab, amino acids are replaced with a different amino acid in at least one position selected from amino acid residues 509, 513, 514, 585, 587, 589, and 590 of SEQ ID NO:2. For Cry1C, amino acids are replaced with a different amino acid in at least one position selected from amino acid residues 508, 509, 510, and 590 of SEQ ID NO:4.

The nucleic acid molecules and mutant pesticidal polypeptides of the present invention find use in methods directed to protecting a plant from an insect pest and for impacting an insect pest. The methods comprise introducing into a plant a polynucleotide construct comprising a nucleic acid molecule of the invention operably linked to a promoter that drives expression in a plant. Expression of the nucleic acid molecule within the plant (e.g., monocot or dicot) will result in the production of a mutant pesticidal polypeptide and confer increased insect resistance to the plant. Accordingly, transgenic (e.g., transformed) plant cells, plant tissues, plants, and seeds thereof comprising a nucleic acid molecule and which express a novel mutant pesticidal polypeptide of the invention are also provided.

The present invention further provides pesticidal compositions and formulations and methods for their use in controlling insect pests. Pesticidal compositions comprise a mutant pesticidal polypeptide of the invention or a transformed microorganism comprising a nucleotide sequence encoding a mutant pesticidal polypeptide of the invention. Methods of using these compositions to impact an insect pest can include applying the pesticidal composition to the environment of the insect pest.

The following embodiments are encompassed by the present invention.

1. A mutant Cry polypeptide having at least one amino acid replacement as compared to a naturally-occurring Cry polypeptide at at least one position selected from the group consisting of positions corresponding to amino acid residues 509, 513, 514, 585, 587, 589, and 590 of SEQ ID NO: 2 and amino acid residues 508, 509, 510, and 590 of SEQ ID NO: 4, wherein said mutant Cry polypeptide has pesticidal activity.

2. The mutant Cry polypeptide of embodiment 1, wherein said polypeptide comprises an amino acid sequence selected from:
   a) an amino acid sequence set forth in SEQ ID NO:2 having at least one amino acid replacement wherein an amino acid residue is replaced with a different amino acid in at least one position selected from residues 509, 513, 514, 585, 587, 589, and 590;
   b) an amino acid sequence having at least 95% sequence identity to the amino acid sequence of (a) wherein said amino acid sequence retains said replacement;
   c) an amino acid sequence having at least 98% sequence identity to the amino acid sequence of (a) wherein said amino acid sequence retains said replacement.

3. The mutant Cry polypeptide of embodiment 2, wherein said amino acid replacement comprises replacing a serine with an alanine at position 509.

4. The mutant Cry polypeptide of embodiment 2, wherein said amino acid replacement comprises replacing a valine with an alanine at position 513.

5. The mutant Cry polypeptide of embodiment 2, wherein said amino acid replacement comprises replacing an asparagine with an alanine, a histidine, or a phenylalanine at position 514.

6. The mutant Cry polypeptide of embodiment 2, wherein said amino acid replacement comprises replacing a threonine with an alanine at position 585.

7. The mutant Cry polypeptide of embodiment 2, wherein said amino acid replacement comprises replacing a serine with an alanine at position 587.

8. The mutant Cry polypeptide of embodiment 2, wherein said amino acid replacement comprises replacing a histidine with an alanine at position 589.

9. The mutant Cry polypeptide of embodiment 2, wherein said amino acid replacement comprises replacing a valine with an alanine at position 590.

10. The mutant Cry polypeptide of embodiment 1, wherein said polypeptide comprises an amino acid sequence selected from:
   a) an amino acid sequence set forth in SEQ ID NO:4 having at least one amino acid replacement wherein an amino acid residue is replaced with a different amino acid in at least one position selected from residues 508, 509, 510, and 590;
   b) an amino acid sequence having at least 95% sequence identity to the amino acid sequence of (a) wherein said amino acid sequence retains said replacement;
   c) an amino acid sequence having at least 98% sequence identity to the amino acid sequence of (a) wherein said amino acid sequence retains said replacement.

11. The mutant Cry polypeptide of embodiment 10, wherein said amino acid replacement comprises replacing a glutamine with an alanine at position 508.

12. The mutant Cry polypeptide of embodiment 10, wherein said amino acid replacement comprises replacing a valine with an alanine at position 509.

13. The mutant Cry polypeptide of embodiment 10, wherein said amino acid replacement comprises replacing an asparagine with an alanine, a histidine, or a pheynlalanine at position 510.

14. The mutant Cry polypeptide of embodiment 10, wherein said amino acid replacement comprises replacing a serine with an alanine at position 590.

15. A polynucleotide having a nucleotide sequence that encodes the mutant Cry polypeptide of any one of embodiments 1-14.

16. An expression cassette comprising the polynucleotide of embodiment 15.

17. The expression cassette of embodiment 16, wherein said polynucleotide is operably linked to a promoter that drives expression in a plant.

18. The expression cassette of embodiment 16, wherein said polynucleotide is operably linked to a promoter that drives expression in a microorganism.

19. A host cell comprising the polynucleotide of embodiment 15 or the expression cassette of any one of embodiments 16-18.

20. A plant comprising the polynucleotide of embodiment 15, wherein said polynucleotide is operably linked to a promoter active in said plant.

21. The plant of embodiment 20, wherein said plant is a monocotyledonous plant.

22. The plant of embodiment 21, wherein said monocotyledonous plant is selected from the group consisting of maize, sugarcane, wheat, rice, barley, sorghum, and rye.

23. The plant of embodiment 22, wherein said monocotyledonous plant is maize.

24. The plant of embodiment 20, wherein said plant is a dicotyledonous plant.

25. A transgenic seed produced by the plant of any one of claims 20-24.

26. A method of protecting a plant from an insect pest, said method comprising introducing into said plant the polynucleotide of embodiment 15, wherein said polynucleotide is operably linked to a promoter that drives expression in said plant.

27. The method of embodiment 26, wherein said pest is a Lepidopteran pest.

28. A pesticidal composition comprising at least one mutant Cry polypeptide of any one of embodiments 1-14.

29. A pesticidal composition of embodiment 28 further comprising a carrier.

30. A microorganism comprising the polynucleotide of embodiment 15, wherein said polynucleotide is operably linked to a promoter active in said microorganism.

31. A pesticidal composition comprising the microorganism of embodiment 30.

32. The pesticidal composition of embodiment 31, further comprising a carrier.

33. A method of protecting a plant from an insect pest comprising applying an effective amount of the pesticidal composition of any one of embodiments 28, 29, 31, and 32 to an environment of the insect pest.

34. The method of embodiment 33, wherein said composition is applied by spraying, dusting, broadcasting, or seed coating.

35. A method for controlling an insect pest in an area of cultivation comprising planting the area with the transgenic seed of embodiment 25.

DETAILED DESCRIPTION OF THE INVENTION

Compositions and methods for protecting a plant from pests, particularly insect pests, are provided. Compositions comprise altered Cry polypeptides. The polypeptides are mutated by replacing or substituting at least one amino acid in domain III, the receptor binding domain. The altered polypeptides display increased toxin activity as well as toxicity against a wider spectrum of insects. Nucleotide sequences encoding altered polypeptides are also provided.

The invention is exemplified by providing altered Cry1Ab and Cry1C polypeptides. However, because of the conserved structure among Cry toxins, similar changes can be made in other Cry toxin polypeptides and such altered polypeptides tested for activity. Mutations or alterations can be made in domain III of the Cry polypeptides, particularly domain III, beta 16 (β16) and beta 22 (β22). Other Cry polypeptides can be aligned with the polypeptides of the invention and mutations made in the amino acid sequence. At least one change can be made at corresponding positions in related Cry polypeptides. That is, at least one of amino acids 508 through 590 can be mutated and replaced with another amino acid. Amino acid changes can be made or introduced and the altered polypeptide tested for activity.

The mutations may increase toxicity of the polypeptide and/or render the polypeptide toxic to additional insect(s). That is, the altered polypeptide may display toxicity to an insect where the native polypeptide shows no toxicity to the insect. Thus, the insect spectrum that is capable of being controlled by the polypeptide is increased.

The presently disclosed polypeptides and polynucleotides are modified from naturally occurring (i.e., found in nature) Cry sequences in that they have at least one amino acid substitution and are referred to herein as "mutant Cry polypeptides" or "mutant Cry polynucleotides". The mutant Cry polypeptides have at least one amino acid substitution as compared to a naturally occurring Cry polypeptide at at least one position selected from the group consisting of positions corresponding to amino acid residues 509, 513, 514, 585, 587, 589, and 590 of SEQ ID NO: 2 and amino acid residues 508, 509, 510, and 590 of SEQ ID NO: 4.

In some embodiments, the mutant Cry polypeptide is a mutant Cry1 polypeptide and thus comprises at least one amino acid substitution at at least one position selected from the group consisting of positions corresponding to amino acid residues 509, 513, 514, 585, 587, 589, and 590 of SEQ ID NO: 2 and amino acid residues 508, 509, 510, and 590 of SEQ ID NO: 4 as compared to a naturally occurring Cry polypeptide within the Cry1 family of polypeptides.

Altered Cry1Ab polypeptides include substitutions within domain III beta 16 and beta 22. In particular, by "mutant or altered Cry1Ab polypeptide" is intended a Cry1Ab polypeptide having at least one amino acid replaced with a different amino acid at one or more of the following positions: amino acid 509, 513, 514, 585, 587, 589, and 590 of SEQ ID NO:2 (the native Cry1Ab sequence, encoded by SEQ ID NO:1; see GenBank Accession No. M13898). Cry1Ab polypeptides with substitutions at one of the positions 509, 513, 514, 585, 587, 589, and 590 displayed toxin activity to *Spodoptera frugiperda*. By "mutant or altered Cry1C polypeptide" is intended a Cry1C polypeptide having at least one amino acid substitution at one of amino acid positions 508, 509, 510, and 590 of SEQ ID NO:4 (the native Cry1C sequence, encoded by SEQ ID NO:3; see GenBank Accession No. AY955268).

The native amino acid of the listed positions can be substituted with any other amino acid and the resulting polypeptide tested for activity against an insect of interest. In one embodiment, the native amino acid is replaced with an alanine. In some positions, the native amino acid is replaced with phenylalanine or histidine.

Bt Cry proteins have five conserved sequence domains, and three conserved structural domains (see, e.g., de Maagd et al. (2001) *Trends Genetics* 17:193-199). The most amino-terminal conserved structural domain (Domain I) consists of seven alpha helices, with a central hydrophobic helix-α5 encircled by six other amphipathic helices, and is involved in membrane insertion and pore formation. The second conserved structural domain (Domain II) consists of three antiparallel beta-sheets implicated in cell binding, and the most carboxy-terminal conserved structural domain (Domain III) consists of a beta-sandwich. Exposed regions in domains II and III are involved in receptor recognition and binding, and are therefore considered determinants of toxin specificity. The location and properties of these domains are known to those of skill in the art. See, for example, Grochulski et al. (1995) *J Mol Biol* 254:447-464; Morse, Yamamoto, and Stroud (2001) *Structure* 9:409-417; Li et al. (1991) *Nature* 353:815-821; Galitsky et al. (2001) *Acta Cryst* D57:1101-1109; Boonserm et al. (2006) *J Bacteriol* 188:3391-3401; Boonserm et al. (2005) *J Mol Biol* 348:363-382; and Guo et al. (2009) *J Struct Biol* 168:259-266. The mutant Cry polypeptides disclosed herein have at least one mutation within Domain III.

Plants, plant cells, seeds, microorganisms, and expression cassettes comprising a nucleotide sequence of the invention that encodes a mutant or altered Cry polypeptide of the invention are also disclosed herein. Pesticidal compositions comprising an isolated mutant pesticidal polypeptide of the invention, or a microorganism that expresses a nucleic acid of the invention, in combination with a carrier are further provided. The compositions of the invention find use in methods for protecting a plant from an insect pest or for impacting an insect pest.

The invention is drawn to the mutant Cry pesticidal polypeptides encoded by the polynucleotides of the present invention and to methods for using such mutant polypeptides. Compositions and formulations comprising a mutant pesticidal polypeptide, or variant or fragment thereof, are useful in methods for impacting an insect pest. "Impact an insect pest" or "impacting an insect pest" is intended to mean, for example, deterring the insect pest from feeding further on the plant, harming the insect pest, or killing the insect pest. The pesticidal polypeptides of the invention can be expressed in a plant or plant part of interest. Likewise, a composition or formulation comprising a mutant pesticidal polypeptide may be applied to the environment of the insect pest. In one embodiment, the mutant pesticidal polypeptide is combined with a carrier for subsequent application to the environment of the insect pest.

One of skill in the art would recognize that the compositions and methods of the invention can be used alone or in combination with other compositions and methods for controlling insect pests that impact plants. For example, the present invention may be used in conjunction with other pesticidal proteins or traditional chemical pesticides.

"Pesticidal gene" or "pesticidal polynucleotide" refers to a nucleotide sequence that encodes a polypeptide that exhibits pesticidal activity. As used herein, the term "pesticidal activity" refers to the ability of a substance, such as a polypeptide, to inhibit the growth, feeding, or reproduction of an insect pest and/or to kill the insect pest. A "pesticidal polypeptide," "pesticidal protein," or "insect toxin" is intended to mean a protein having pesticidal activity.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. In this manner, pesticidal activity impacts at least one measurable parameter of pest fitness. As used herein, "pest" means an organism that interferes with or is harmful to plant development and/or growth.

Assays for assessing pesticidal activity are well known in the art. See, e.g., U.S. Pat. Nos. 6,570,005 and 6,339,144. See, e.g., U.S. Pat. Nos. 6,570,005 and 6,339,144. See also Brooke et al. (2001) *Bull. Entomol. Res.* 91:265-272; Chen et al. (2007) *Proc. Natl. Acad. Sci. USA* 104:13901-13906; Crespo et al. (2008) *Appl. Environ. Microb.* 74:130-135; Khambay et al. (2003) *Pest Manag. Sci.* 59:174-182; Liu & Dean (2006) *Protein Eng. Des. Sel.* 19:107-111; Marrone et al. (1985) *J. Econ. Entomol.* 78:290-293; Robertson et al., Pesticide Bioassays with Arthropods ($2^{nd}$ ed., CRC Press 2007); Scott & McKibben (1976) *J. Econ. Entomol.* 71:343-344; Stickman (1985) *Bull. Environ. Contam. Toxicol.* 35:133-142; and Verma et al. (1982) *Water Res.* 16 525-529; as well as U.S. Pat. No. 6,268,181. Examples of insect bioassays include, but are not limited to, pest mortality, pest weight loss, pest repellency, pest attraction, and other behavioral and physical changes of the pest after feeding and exposure to a pesticide or pesticidal polypeptide for an appropriate length of time. General methods include addition of the pesticide, pesticidal polypeptide or an organism having the pesticidal polypeptide to the diet source in an enclosed container. See, e.g., U.S. Pat. Nos. 6,339,144 and 6,570,005. Pesticidal activity can be measured by, but is not limited to, changes in mortality, weight loss, attraction, repellency and other behavioral and physical changes after feeding and exposure for an appropriate length of time.

The preferred developmental stage for testing for pesticidal activity is larvae or immature forms of these above-mentioned insect pests. The insects may be reared in total darkness at from about 20° C. to about 30° C. and from about 30% to about 70% relative humidity. Bioassays may be performed as described in Czapla and Lang (1990) *J. Econ. Entomol.* 83(6):2480-2485. Methods of rearing insect larvae and performing bioassays are well known to one of ordinary skill in the art.

A wide variety of bioassay techniques for assessing pesticidal activity is known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time.

A polypeptide having "improved pesticidal activity" or "improved pesticidal activity" can refer to a polypeptide exhibiting an increase in activity against a single plant pest or activity against a wider spectrum of plant pests as compared to a reference polypeptide (e.g., naturally occurring Cry polypeptide). In some embodiments, the presently disclosed mutant Cry pesticidal polypeptides or variants or fragments thereof display improved pesticidal activity when compared to a naturally occurring Cry polypeptide (e.g., SEQ ID NO: 2 or 4). In certain embodiments, the presently disclosed mutant Cry pesticidal polypeptide exhibits a 2-fold to 100-fold greater activity against at least one susceptible insect pest than a naturally occurring Cry polypeptide (e.g., SEQ ID NO: 2 or 4), including but not limited to, about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 50-fold, 60-fold, 70-fold, 80-fold, 90-fold, and 100-fold. A finding of improved or enhanced pesticidal activity requires a demonstration of an increase of pesticidal activity of at least 10%, against the pest target, or at least 20%, 25%, 30%, 35%, 40%, 45%, 50%, 60%, 70%, 100%, 150%, 200%, or 300% or greater increase of pesticidal activity relative to the pesticidal activity of a naturally occurring polypeptide as determined against the same pest.

In certain embodiments, a presently disclosed mutant Cry pesticidal polypeptide or variant or fragment thereof exhibits greater pesticidal activity against a Lepidopteran pest when compared to a naturally occurring Cry (e.g., SEQ ID NO: 2 or 4). In some of these embodiments, the mutant Cry polypeptide has greater pesticidal activity against at least one of tobacco hornworm (*Manduca sexta*) and fall armyworm (*Spodoptera frugiperda*) when compared to a naturally occurring Cry polypeptide (e.g., SEQ ID NO: 2 or 4).

The invention encompasses isolated or substantially purified polynucleotide or polypeptide compositions. An "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The proteins of the invention may have additional alterations including amino acid substitutions, deletions, truncations, and insertions. Methods for such manipulations are generally known in the art. For example, amino acid sequence variants and fragments of the pesticidal proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

The variants of the mutant Cry proteins will continue to possess the desired pesticidal activity. Obviously, the mutations that will be made in the DNA encoding the variant must not place the sequence out of reading frame and optimally will not create complementary regions that could produce secondary mRNA structure. See, EP Patent Application Publication No. 75,444. When it is difficult to predict the exact effect of the substitution, deletion, or insertion in advance of doing so, one skilled in the art will appreciate that the effect will be evaluated by routine screening assays. That is, the activity of a pesticidal polypeptide can be evaluated by, for example, insect-feeding assays. See, e.g., Marrone et al. (1985) *J. Econ. Entomol.* 78:290-293 and Czapla and Lang (1990) supra, herein incorporated by reference.

Variants and fragments of the mutant Cry sequences are encompassed by the present invention. By "variant" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the mutant Cry polynucleotide. For polynucleotides, conservative variants will encode the amino acid sequence of the mutant Cry protein. Generally, variants of a particular mutant polynucleotide of the invention will have at least about 80%, about 90%, about 95%, about 96%, about 97%, about 98% or about 99% sequence identity to the reference polynucleotide as determined by sequence alignment programs and parameters described herein.

"Variant" polypeptide is intended to mean a protein derived from a mutant Cry protein or a fragment thereof by deletion (so-called truncation) of one or more amino acids at the N-terminal and/or C-terminal end of the native protein; deletion or addition of one or more amino acids at one or more internal sites in the native protein; and/or substitution of one or more amino acids at one or more sites in the native protein. Variant polypeptides encompassed by the present invention are biologically active, that is they continue to possess the desired biological activity of the mutant Cry protein.

In general, biologically active variants of a polypeptide of the invention will have at least about 85%, 86%, 87%, 88%, 89%, 90%, 91%, 92%, 93%, 94%, 95%, about 96%, about 97%, about 98%, about 99% or more sequence identity to the amino acid sequence for the native protein, as determined by sequence alignment programs and parameters described elsewhere herein. A biologically active variant of a protein of the invention may differ from that protein by as few as 1-15 amino acid residues, as few as 1-10, as few as 6-10, as few as 5, as few as 4, 3, 2, or even 1 amino acid residue(s).

As used herein the term "fragment" refers to a portion of a nucleotide sequence of a polynucleotide or a portion of an amino acid sequence of a polypeptide of the invention. Fragments of a nucleotide sequence may encode protein fragments that retain the biological activity of the native or corresponding full-length protein and hence possess the relevant biological activity such as pesticidal activity.

Nucleic acids that are fragments of a mutant Cry nucleotide sequence comprise at least 16, 20, 50, 75, 100, 150, 200, 250, 300, 350, 400, 450, 500, 600, 700, 800, 1,000, 1,200, 1,400, 1,600, 1,800, or 1900 nucleotides, or up to the number of nucleotides present in the mutant Cry nucleotide sequences disclosed herein. In particular embodiments, the nucleic acids of the invention disclose fragments derived from (e.g., produced from) a nucleic acid of the invention, wherein the fragment encodes a truncated mutant Cry endotoxin characterized by pesticidal activity. The truncated polypeptide encoded by the polynucleotide fragments of the invention are characterized by pesticidal activity that is either equivalent to, or improved, relative to the activity of the corresponding full-length polypeptide encoded by the nucleic acid from which the fragment is derived. In some embodiments, nucleic acid fragments of the invention are truncated at the 3' end of the native or corresponding full-length coding sequence. Nucleic acid fragments may also be truncated at both the 5' and 3' end of the native or corresponding full-length coding sequence.

Furthermore, it is understood that the invention also encompasses polypeptides that are fragments of the exemplary pesticidal proteins of the invention and having lengths of at least about 100, about 200, about 300, about 400, about 500, about 600, about 700, about 800, about 900, about 1000, about 1044, about 1100, or about 1155 contiguous amino acids of a pesticidal polypeptide of the invention and retain pesticidal activity.

The variants and fragments of the mutant Cry polynucleotides and polypeptides will retain the substituted amino acids discussed above. That is, for Cry1Ab, the variant polypeptide will comprise at least one amino acid substitution at positions 509, 512, 513, 514, 585, 587, 589, and 590 of SEQ ID NO:2. Cry1C variants will comprise at least one amino acid substitution at positions 508, 509, 510, and 590 of SEQ ID NO:4.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997), supra. When utilizing BLAST, Gapped BLAST, PSI-BLAST, the default parameters of the respective programs (e.g., BLASTN for nucleotide sequences, BLASTX for proteins) can be used. See ncbi.nlm.nih.gov on the World Wide Web. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, an amino acid residue of a mutant Cry polypeptide at the position corresponding to a particular amino acid residue of a naturally occurring Cry (e.g., SEQ ID NO: 2 or 4) refers to the amino acid residue within the mutant Cry polypeptide that appears opposite the amino acid residue at a particular position in the naturally occurring Cry sequence when the mutant Cry sequence is aligned with the naturally occurring Cry sequence (e.g., SEQ ID NO: 2 or 4) for maximum homology using an alignment program, such as one known in the art or one described herein.

The polynucleotides of the present invention can be expressed in a host cell, such as a bacterial, fungal, yeast, insect, mammalian, or preferably plant cells. The term "host cell" as used herein refers to a cell which contains a vector and supports the replication and/or expression of the expression vector is intended. Host cells may be prokaryotic cells, such as Bacillus spp., or eukaryotic cells, such as yeast, insect, or plant cells. In some embodiments, host cells are monocotyledonous or dicotyledonous plant cells.

Mutant pesticidal polynucleotides of the invention can be provided in expression cassettes for expression in the host cell of interest. The cassette will include 5' and 3' regulatory sequences operably linked to a pesticidal polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of a polynucleotide of the invention to be under the transcriptional regulation of the regulatory regions. The expression cassette may additionally contain selectable marker genes.

The expression cassette will include in the 5'-3' direction of transcription, a transcriptional and translational initiation region functional in the host cell (i.e., a promoter), a pesticidal polynucleotide of the invention, and a transcriptional and translational termination region (i.e., termination region) functional in the host cell. The regulatory regions (i.e., promoters, transcriptional regulatory regions, and translational termination regions) and/or the polynucleotide of the invention may be native/analogous to the host cell or to each other. Alternatively, the regulatory regions and/or the pesticidal polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence. While it may be optimal to express the sequences using heterologous promoters, the native promoter sequences may be used.

The termination region may be native with the transcriptional initiation region, may be native with the operably linked pesticidal polynucleotide of interest, may be native with the plant host, or may be derived from another source (i.e.; foreign or heterologous to the promoter, the polynucleotide of interest, the host cell, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol. Bioeng.* 85:610-9 and Fetter et al. (2004) *Plant Cell* 16:215-28), cyan fluorescent protein (CYP) (Bolte et al. (2004) *J Cell Science* 117:943-54 and Kato et al. (2002) *Plant Physiol.* 129:913-42), and yellow fluorescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon, pp.* 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) *Ph.D. Thesis*, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) *Ph.D. Thesis*, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et at (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the present invention in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Tissue-preferred promoters can be utilized to target enhanced pesticidal protein expression within a particular plant tissue, particularly within a tissue that is likely to be the target of pest attack. In particular embodiments, a pesticidal polypeptide is selectively expressed in tissues where insect-related damage is likely to occur. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2): 513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J* 4(3):495-505.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. Other root-preferred promoters of interest are disclosed in U.S. patent application Ser. No. 11/022,111, entitled "Maize Metallothionein Promoter," filed Dec. 22, 2004, and U.S. patent application Ser. No. 11/022,449, entitled "Maize Metallothionein 2 Promoter and Methods of Use," filed Dec. 22, 2004, both of which are herein incorporated by reference in their entirety.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Ciml (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

In particular aspects, methods for protecting a plant from an insect pest comprise introducing into a plant at least one polynucleotide, wherein the polynucleotide comprises a nucleotide sequence encoding a mutant pesticidal polypeptide of the invention. The polynucleotide is operably linked to a promoter that drives expression in the plant. The plant expresses the mutant pesticidal polypeptide, thereby exposing the insect pest to the polypeptide at the site of insect attack. Expression of a mutant pesticidal polypeptide of the invention may be targeted to specific plant tissues where pesticidal activity is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

Just as expression of a mutant pesticidal polypeptide of the invention may be targeted to specific plant tissues or cell types through the use of appropriate promoters, it may also be targeted to different locations within the cell through the use of targeting peptides. Depending on the metabolic function of the tissue or cell type, the location of the protein in different compartments of the cell may make it more efficacious against a given pest or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pest and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location.

Other pests may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art and include, for example, KDEL (SEQ ID NO: 5), SEKDEL (SEQ ID NO: 6), HDEL (SEQ ID NO: 7), and HDEF (SEQ ID NO: 8). See, for example, Denecke et al. (1992). *EMBO J.* 11:2345-2355; Wandelt et al. (1992) *Plant J* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481. Chloroplast targeting sequences that encode such transit peptides are also known in the art and include the chloroplast small subunit of ribulose-1,5-bisphosphate carboxylase (Rubisco) (de Castro Silva Filho et al. (1996) *Plant Mol. Biol.*

30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). A person skilled in the art could also envision generating transgenic plants in which the chloroplasts have been transformed to overexpress a gene for a pesticidal peptide. See, for example, Daniell (1999) *Nature Biotech* 17:855-856; and U.S. Pat. No. 6,338,168.

One could also envision localizing the pesticidal polypeptide in other cellular compartments by addition of suitable targeting information. (Raikhel and Chrispeels, supra). A useful site available on the world wide web that provides information and references regarding recognition of the various targeting sequences can be found at: psort.nibb.ac.jp/mit. Other references regarding the state of the art of protein targeting include Silva-Filho (2003) *Curr. Opin. Plant Biol.* 6:589-595; Nicchitta (2002) *Curr. Opin. Cell Biol.* 14:412-416; Bruce (2001) *Biochim Biophys Acta* 1541: 2-21; Hadlington & Denecke (2000) *Curr. Opin. Plant Biol.* 3: 461-468; Emanuelsson et al. (2000) *J. Mol. Biol.* 300: 1005-1016; Emanuelsson & von Heijne (2001) *Biochim Biophys Acta* 1541: 114-119, herein incorporated by reference.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the nucleotide sequences of the invention can be provided to a plant using a variety of transient transformation methods. Such transient transformation methods include, but are not limited to, the introduction of the pesticidal protein or variants and fragments thereof directly into the plant or the introduction of the pesticidal polypeptide transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci. USA* 91:2176-2180 and Hush et al. (1994) *J. Cell Science* 107:775-784, all of which are herein incorporated by reference. Alternatively, the pesticidal polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which is released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the a pesticidal polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191; 5,889,190; 5,866,785; 5,589,367; 5,316,931; and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO 99/25821, WO 99/25854, WO 99/25840, WO 99/25855, and WO 99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site that is flanked by two non-recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 99/25821, WO 99/25854, WO 99/25840, WO 99/25855, and WO 99/25853, all of which are herein incorporated by reference.

As used herein, the term plant also includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation and protection of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine* max), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus carica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, Brassica, soybean, cotton, safflower, peanut, sorghum, wheat, millet, tobacco, etc.). In other embodiments, corn, soybean, and sugarcane plants are optimal, and in yet other embodiments, corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A gene encoding a mutant pesticidal polypeptide of the invention may be introduced into any suitable microbial host according to standard methods in the art. For example, microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, and to provide for stable maintenance and expression of the gene expressing the mutant pesticidal protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

Other illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *photobacterium, Zymomonas, Serratia, Aeromonas, Vibrio, Desulfovibrio*, and *Spirillum*; Lactobacillaceae; Pseudomonadaceae, such as *Pseudomonas* and *Acetobacter*; Azotobacteraceae; and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Genes encoding the pesticidal polypeptides of the invention can be introduced into microorganisms that multiply on plants (epiphytes) to deliver pesticidal proteins to potential target pests. Epiphytes, for example, can be gram-positive or gram-negative bacteria.

Genes encoding mutant pesticidal proteins can be introduced, for example, into microorganisms, such as *Bacillus*, by means of electrotransformation. Specifically, genes encoding the pesticidal proteins can be cloned into a shuttle vector, for example, pHT3101 (Lerecius et al. (1989) *FEMS Microbiol. Letts.* 60:211-218. The shuttle vector pHT3101 containing the coding sequence for the particular pesticidal gene can, for example, be transformed into the *Bacillus* by means of electroporation (Lerecius et al. (1989) *FEMS Microbiol. Letts.* 60:211-218).

Pesticidal compositions are also encompassed by the present invention. Pesticidal compositions may comprise mutant pesticidal polypeptides of the invention or microorganisms comprising and expressing a nucleotide sequence that encodes a mutant pesticidal polypeptide of the invention. The pesticidal compositions of the invention may be applied to the environment of a plant pest, as described herein below, thereby protecting a plant from a plant pest. Moreover, a pesticidal composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Methods are provided for protecting a plant from a plant pest comprising applying an effective amount of a pesticidal protein or composition of the invention to an environment of the pest. By "effective amount" is intended an amount of a protein or composition sufficient to control a plant pest.

Mutant pesticidal proteins and compositions can be applied to the environment of the pest by methods known to those of ordinary skill in the art.

The pesticidal compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins of the present invention, more particularly Cry toxins, of the present invention include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The pesticidal compositions of the present invention can be in a suitable form for direct application or as a concentrate of primary composition that requires dilution with a suitable quantity of water or other diluent before application. The concentration of the pesticidal polypeptide will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb.-5.0 lb. per acre when in dry form and at about 0.01 pts.-10 pts. per acre when in liquid form.

In a further embodiment, the compositions, as well as the transformed microorganisms and mutant pesticidal proteins, of the invention can be treated prior to formulation to prolong the pesticidal activity when applied to the environment of a target pest as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.)).

In other embodiments of the invention, it may be advantageous to treat the mutant Cry polypeptides with a protease, for example trypsin, to activate the protein prior to application of a pesticidal protein composition of the invention to the environment of the target pest. Methods for the activation of protoxin by a serine protease are well known in the art. See, for example, Cooksey (1968) *Biochem. J.* 6:445-454 and Carroll and Ellar (1989) *Biochem. J.* 1 261:99-105, the teachings of which are herein incorporated by reference. For example, a suitable activation protocol includes, but is not limited to, combining a polypeptide to be activated, for example a purified mutant Cry polypeptide and trypsin at a 1/100 weight ratio of mutant Cry protein/trypsin in 20 nM NaHCO$_3$, pH 8 and digesting the sample at 36° C. for 3 hours.

The pesticidal compositions of the invention can be applied to the environment of a plant pest, a plant, a plant seed, plant part, or an area of cultivation by, for example, spraying, atomizing, dusting, scattering, coating or pouring, introducing into or on the soil, introducing into irrigation water, by seed treatment or general application or dusting at the time when the pest has begun to appear or before the appearance of the pest as a protective measure. For example, the mutant pesticidal protein and/or transformed microorganisms of the invention may be mixed with grain to protect the grain during storage. It is generally important to obtain good control of pest in the early stages of plant growth, as this is the time when the plant can be most severely damaged. In one embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, an herbicide, an insecticide, a fertilizer, an inert carrier, and dead cells of a *Bacillus* strain or transformed microorganism of the invention.

Compositions of the invention find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

The pesticidal composition can be applied to an area of cultivation before or after planting. The area of cultivation can comprise the insect pest or the environmental conditions of the area of cultivation can be conducive to the insect pest (e.g., preferred air temperature, season, soil temperature for growth of the insect pest). As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods and compositions of the present invention may be effective against a variety of pests. Pests include insects of the order Lepidoptera, including but not limited to, armyworms, cutworms, loopers, and heliothines in the family Noctuidae; *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (Xylomyges) *curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leafier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermiiller (European grape vine moth); *Platynota flavedana* Clemens (variegated leafroller); *P. stultana* Walsingham (omnivorous leafroller); *Spilonota ocellana* Denis & Schiffermiiller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis* subflexa Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

The article "a" and "an" are used herein to refer to one or more than one (i.e., to at least one) of the grammatical object of the article. By way of example, "an element" means one or more element.

The following examples are provided by way of illustration, not by way of limitation.

EXPERIMENTAL

Example 1

Assaying the Pesticidal Activity of Cry1 Mutant Polypeptides

Domain II and domain III have been recognized as the receptor binding domains for Cry proteins. Regarding domain III, the mapping of epitopes recognized by monoclonal antibodies that compete for binding of Cry1Aa with *Bombix mori* aminopeptidase N (APN) has demonstrated that in domain III β16 ($^{508}$STLRVN$^{513}$; SEQ ID NO:9) and β22 ($^{582}$VFTLSAHV$^{589}$; SEQ ID NO:10) residues that are exposed and in close proximity to the 3-dimensional structure are involved in the Cry1Aa-APN interaction. Similar experiments have revealed that Cry1Ab also binds APN through similar amino acid regions in *M. sexta*. In order to analyze the effect of specific Cry1Ab residues for APN binding and toxicity, β16 ($^{506}$GQISTLRVNITA$^{517}$; SEQ ID NO:11) and β22 ($^{583}$VFTLSAHVFN$^{592}$; SEQ ID NO:12) residues were subjected to alanine substitutions. Tables 1 and 2 show the insecticidal activities of the mutant polypeptides that were stable and produced in *Bacillus thuringiensis*. As demonstrated in Table 1, L511A was not toxic to *M. sexta*. Several Cry1Ab domain III mutants such as S509A, V513A, N514A, T585A, S587A, H589A, and V590A gained toxicity to *S. frugiperda* relative to wild-type Cry1Ab polypeptide. Among these, S509A, V513A, and N514A retained significant activity against *M. sexta*. Of the Cry1Ab domain III β16 mutants (Table 1), N514A was the most active toxin against *S. frugiperda* with a level of activity similar to that of Cry1C (LC$_{50}$ of 163 (92-250) ng/cm$^2$). Two of the Cry1Ab domain III β22 mutants (T585A and S587A mutants) showed enhanced toxicity with even higher toxicity than previous β16 mutants (Table 2).

TABLE 1

Toxicity of Cry1Ab Domain III β16 Mutants*

| | LC$_{50}$ (ng/cm$^2$) | |
|---|---|---|
| | Manduca sexta | Spodoptera frugiperda |
| WT Cry1Ab (SEQ ID NO: 2) | 3.7 (1.6-6.9) | >5000 |
| S509A | 5.7 (4.6-7.2) | 526 (381-751) |
| T510A | 31.9 (14.7-201.7) | >5000 |
| L511A | >1000 | >5000 |
| R512A | 6.5 (5-9) | >5000 |
| V513A | 45 (26-105) | 393 (296-523) |
| N514A | 15.3 (10.3-25.7) | 149 (101-204) |

*Substitutions at each amino acid position are relative to the residue number in SEQ ID NO: 2

TABLE 2

Toxicity of Cry1Ab Domain III β22 Mutants*

| | LC$_{50}$ (ng/cm$^2$) Spodoptera frugiperda |
|---|---|
| V583A: | 98 |
| F584A: | 350 |
| T585A: | 59 |
| L586A: | >1000 |
| S587A: | 26 |
| H589A: | 202 |
| V590A: | 277 |

*Substitutions at each amino acid position are relative to the residue number in SEQ ID NO: 2

In order to analyze the effect of specific Cry1C residues for APN binding and toxicity, β16 and β22 residues were subjected to alanine substitutions. Tables 3 and 4 show the insecticidal activities of the mutant polypeptides that were stable and produced in *Bacillus thuringiensis*. As demonstrated in Table 3, V505A and S506A were not toxic to *Spodoptera frugiperda*. Cry1C domain III β16 mutants V509A and N510A gained toxicity to *S. frugiperda* relative to wild-type Cry1C polypeptide. The CryC domain III β22 mutant showed 8-fold higher activity against *S. frugiperda* relative to wild-type Cry1C polypeptide (Table 4).

TABLE 3

Toxicity of Cry1C Domain III β16 Mutants*

| | LC$_{50}$ (ng/cm$^2$) | |
|---|---|---|
| | Manduca sexta | Spodoptera frugiperda |
| WT Cry1C (SEQ ID NO: 4) | 25 (18-35) | 255 (185-348) |
| V505A | 44 (27-100) | >2500 |
| S506A | 90 (56-222) | >2500 |
| L507A | 42 (27-83) | 335 (250-444) |
| Q508A | 43 (30-70) | 241 (141-416) |
| V509A | 16 (11-22) | 118 (36-218) |
| N510A | 33 (25-45) | 65 (43-95) |

*Substitutions at each amino acid position are relative to the residue number in SEQ ID NO: 4

TABLE 4

Toxicity of Cry1C Domain III β22 Mutants*

| | LC$_{50}$ (ng/cm$^2$) Spodoptera frugiperda |
|---|---|
| WT Cry1C (SEQ ID NO: 4) | 250 (55-777) |
| S590A | 32 (16-55) |

*Substitutions at each amino acid position are relative to the residue number in SEQ ID NO: 4

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A mutant Cry polypeptide having at least 95% identity to SEQ ID NO: 2 or SEQ ID NO: 4 and at least one amino acid replacement as compared to the naturally-occurring Cry polypeptide of SEQ ID NO: 2 or SEQ ID NO: 4 at at least one position selected from the group consisting of positions corresponding to amino acid residues 509, 513, 514, 585, 587, 589, and 590 of SEQ ID NO: 2 or amino acid residues 508, 509, 510, and 590 of SEQ ID NO: 4, wherein said mutant Cry polypeptide has increased pesticidal activity against *Spodoptera frugiperda* or *Manduca sexta* compared to wild-type Cry1Ab of SEQ ID NO: 2 or wild-type Cry1C of SEQ ID NO: 4.

2. The mutant Cry polypeptide of claim 1, wherein said polypeptide comprises an amino acid sequence having at least 98% sequence identity to the amino acid sequence of SEQ ID NO: 2, wherein said amino acid sequence retains said replacement.

3. The mutant Cry polypeptide of claim 1, wherein said amino acid replacement comprises replacing the serine with an alanine at position 509 of SEQ ID NO: 2.

4. The mutant Cyr polypeptide of claim 1, wherein said amino acid replacement comprises replacing the valine with an alanine at position 513 of SEQ ID NO: 2.

5. The mutant Cyr polypeptide of claim 1, wherein said amino acid replacement comprises replacing the asparagine with an alanine, a histidine, or a phenylalanine at position 514 of SEQ ID NO: 2.

6. The mutant Cry polypeptide of claim 1, wherein said amino acid replacement comprises replacing the threonine with an alanine at position 585 of SEQ ID NO: 2.

7. The mutant Cry polypeptide of claim 1, wherein said amino acid replacement comprises replacing the serine with an alanine at position 587 of SEQ ID NO: 2.

8. The mutant Cry polypeptide of claim 1, wherein said amino acid replacement comprises replacing the histidine with an alanine at position 589 of SEQ ID NO: 2.

9. The mutant Cry polypeptide of claim 1, wherein said amino acid replacement comprises replacing the valine with an alanine at position 590 of SEQ ID NO: 2.

10. The mutant Cry polypeptide of claim 1, wherein said polypeptide comprises an amino acid sequence having at least 98% sequence identity to the amino acid sequence of SEQ ID NO: 4 wherein said amino acid sequence retains said replacement.

11. The mutant Cry polypeptide of claim 1, wherein said amino acid replacement comprises replacing the glutamine with an alanine at position 508 of SEQ ID NO: 4.

12. The mutant Cry polypeptide of claim 1, wherein said amino acid replacement comprises replacing the valine with an alanine at position 509 of SEQ ID NO: 4.

13. The mutant Cry polypeptide of claim 1, wherein said amino acid replacement comprises replacing the asparagine with an alanine, a histidine, or a phenylalanine at position 510 of SEQ ID NO: 4.

14. The mutant Cry polypeptide of claim 1, wherein said amino acid replacement comprises replacing the serine with an alanine at position 590 of SEQ ID NO: 4.

15. A polynucleotide having a nucleotide sequence that encodes the mutant Cry polypeptide of claim 1.

16. An expression cassette comprising the polynucleotide of claim 15.

17. The expression cassette of claim 16, wherein said polynucleotide is operably linked to a promoter that drives expression in a plant.

18. The expression cassette of claim 16, wherein said polynucleotide is operably linked to a promoter that drives expression in a microorganism.

19. A host cell comprising the polynucleotide of claim 15.

20. A plant comprising the polynucleotide of claim 15, wherein said polynucleotide is operably linked to a promoter active in said plant.

21. The plant of claim 20, wherein said plant is a monocotyledonous plant.

22. The plant of claim 21, wherein said monocotyledonous plant is selected from the group consisting of maize, sugarcane, wheat, rice, barley, sorghum, and rye.

23. The plant of claim 22, wherein said monocotyledonous plant is maize.

24. The plant of claim 20, wherein said plant is a dicotyledonous plant.

25. A transgenic seed produced by the plant of claim 20.

26. A method of protecting a plant from an insect pest, said method comprising introducing into said plant the polynucleotide of claim 15, wherein said polynucleotide is operably linked to a promoter that drives expression in said plant.

27. The method of claim 26, wherein said pest is a Lepidopteran pest.

28. A pesticidal composition comprising the mutant Cry polypeptide of claim 1.

29. The pesticidal composition of claim 28 further comprising a carrier.

30. A microorganism comprising the polynucleotide of claim 15, wherein said polynucleotide is operably linked to a promoter active in said microorganism.

31. A pesticidal composition comprising the microorganism of claim 30.

32. The pesticidal composition of claim 31, further comprising a carrier.

33. A method of protecting a plant from an insect pest comprising applying an effective amount of the pesticidal composition of claim 28 to an environment of the insect pest.

34. The method of claim 33, wherein said composition is applied by spraying, dusting, broadcasting, or seed coating.

35. A method of protecting a plant from an insect pest comprising applying an effective amount of the pesticidal composition of claim 31 to an environment of the insect pest.

36. The method of claim 35, wherein said composition is applied by spraying, dusting, broadcasting, or seed coating.

37. A method for controlling an insect pest in an area of cultivation comprising planting the area with the transgenic seed of claim 25.

* * * * *